United States Patent [19]
Dennis et al.

[11] Patent Number: 4,550,461
[45] Date of Patent: Nov. 5, 1985

[54] BIPLANE POSTING DEVICE

[76] Inventors: Kenrick J. Dennis, 376 Orange St., Oakland, Calif. 94610; Robert A. Cooke, 341 Century Cir., Danville, Calif. 94526

[21] Appl. No.: 573,281

[22] Filed: Jan. 23, 1984

[51] Int. Cl.⁴ .......................... A43D 39/00; A61F 5/14
[52] U.S. Cl. ................................ 12/1 R; 12/146 M; 12/142 N; 128/80 DB
[58] Field of Search ..................... 12/1 R, 1 G, 142 Q, 12/142 N, 146 M, 17 R, 38, 20, 20.2, 21, 31.5; 36/88; 128/80 DB, 779, 584, 585, 595, 80 R; 425/119, 129 S; 33/3 R, 3 A, 3 B, 3 C

[56] References Cited

U.S. PATENT DOCUMENTS

| | | | |
|---|---|---|---|
| 1,120,489 | 12/1914 | Hilgert | 12/142 N |
| 2,492,059 | 12/1949 | Ogden | 128/80 DB |
| 2,714,770 | 8/1955 | Murray | 128/595 |
| 3,072,934 | 1/1963 | Bernier | 12/142 N |
| 3,825,017 | 7/1974 | Scrima | 128/595 |

FOREIGN PATENT DOCUMENTS 146605  3/1936  Fed. Rep. of Germany ... 12/146 M

OTHER PUBLICATIONS

"Paying Through the Feet", Higdon, The Runner, Nov. 1982, pp. 86–90.

*Primary Examiner*—Werner H. Schroeder
*Assistant Examiner*—Steven N. Meyers
*Attorney, Agent, or Firm*—Manfred M. Warren; Robert B. Chickering; Glen R. Grunewald

[57] ABSTRACT

A biplanar posting device having a board with a rear edge and a front edge and lines passing from the rear edge toward the front edge diverging toward the front edge and intersecting the front edge at an angle of about 70 degrees with a plate fixed to the upper surface of the board having end planar portions held in contact with the board and central diverging portions in the form of two flat planes diverging from the upper surface of the board at about 4 degrees and intersecting the planes in contact with the board at a line that overlays the diverging lines. An orthotic properly placed on the device and packed with plastic beneath the heel portion will inherently be formed with a lower surface to correct a defect in the bones of a patient.

9 Claims, 3 Drawing Figures

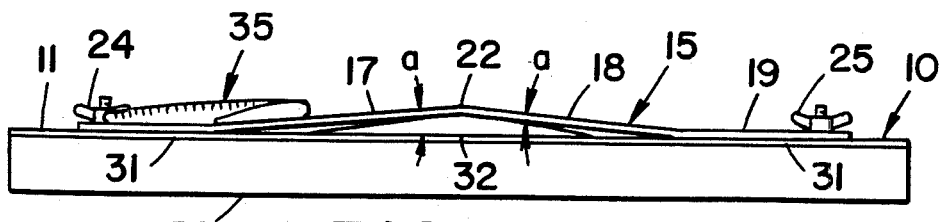
FIG_1
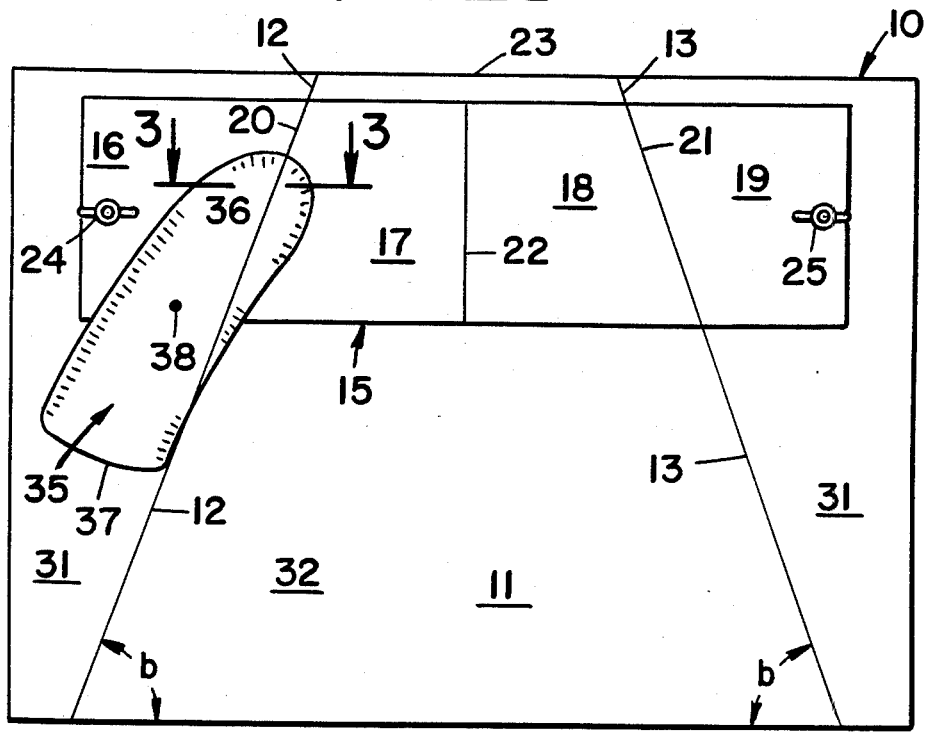
FIG_2
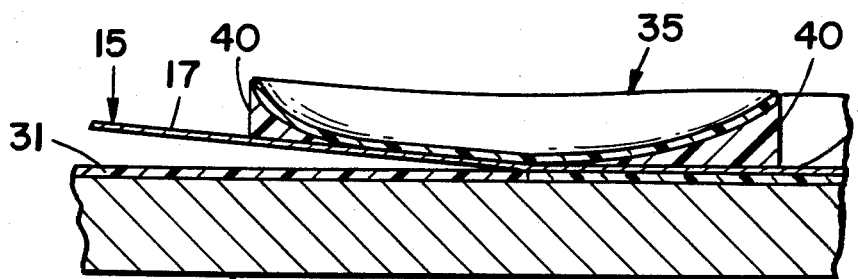
FIG_3

BIPLANE POSTING DEVICE

FIELD OF THE INVENTION

This invention is in the field of manufacturing orthotics used in the practice of podiatry.

BACKGROUND OF THE INVENTION

Bones and muscles of the legs and feet are adapted to absorb the forces generated during the walking and running gait cycle. These forces are referred to as shock. Particularly the foot has many adaptations for absorbing shock. The long arch and metatarsal arch of the foot play an important role in absorbing shock but the motion of the heel is extremely important. Motion of the heel not only absorbs shock but it plays an important role in locking and unlocking other joints which absorb much of the force of walking and running and which influence the ability to propel oneself in walking and running.

In order for the heel to move properly, also called pronation, during a stride the heel should strike the ground on the outside portion of the heel and it should rotate approximately 4 degrees inwardly during the time the foot is in contact with the ground. Rotation should be such that the ankle moves inward or toward the other ankle. Such rotation, as mentioned above, absorbs shock and adjusts the attitude of other joints and muscles to absorb shock.

A common disorder is for the legs and feet to be oriented so that the back of the heel or even the inside of the heel first strikes the ground during a stride so that rotation or pronation does not occur, or occurs to too small a degree, or occurs in a direction that does not perform the functions of orienting the rest of the skeleton and musculature to absorb shock.

This condition is normally treated by providing patients with devices called orthotics. Orthotics are usually in the form of thermo-plastic devices which fit into the shoes. The upper surface of an orthotic is made to conform to the shape of the appropriate portions of the patient's foot, usually by being heated to a plastic condition and solidified while held against a cast of the patient's foot. The orthotic normally has a shallow heel cup and extends forward to about the metatarsal arch.

After the upper surface of the orthotic is formed a plastic base or post is formed beneath the heel cup from a suitable material such as polymethylmethacrylate, after which the bottom of the heel-like post is ground to have two intersecting planes. The planes should intersect on a line between a point approximately 5 millimeters inwardly from the rearmost extension of the heel cup to a point tangent with the outermost and forwardmost portion of the orthotic. The planes should intersect at an angle of 4 degrees for the usual case although other angles may be employed for persons having greater or lesser needs for such correction.

Customarily, orthotics are prepared by obtaining a plaster cast of the patient's foot to obtain an impression of the contours of the patient's foot and then sending that contoured cast to a laboratory where a thermoplastic sheet is molded to the cast. The rear post portion is then attached and ground to provide the proper intersecting planes. Preparing the rear post requires expensive and highly skilled handwork to grind two intersecting planes at the correct angle with respect to each other and to have those planes intersect on a line between a particular point at the heel of the orthotic and a tangent to the edge. In addition, the preparation of orthotics by laboratory technicians causes a delay in the patient obtaining the orthotic due to the transportation time between the podiatrist's office and the laboratory and, of course, the time required to actually do the work.

SUMMARY OF THE INVENTION

This invention is a device for preparing an orthotic to have a post with the exact orientation with respect to the relationship of the intersecting planes and the direction of the line of intersection between them. The device of this invention prepares posts having their bottoms perfectly shaped without grinding or other handwork. Using the device of this invention, at most, the vertical sides of a post need to be trimmed but the trimming of the vertical sides has nothing to do with the function but only with cosmetics and can be done quickly, without expensive equipment, and in the office of a podiatrist or physician. By employing the device of this invention, orthotics can be prepared at small expense while a patient waits and yet the orthotic is perfectly formed to a degree of perfection that could not be bettered by a highly skilled technician.

BRIEF DESCRIPTION OF THE DRAWINGS

FIG. 1 is an elevation view of a device embodying this invention with an orthotic positioned on it for mounting a post beneath the heel portion.

FIG. 2 is a plan view of FIG. 1.

FIG. 3 is a section along the line 3—3 of FIG. 2 illustrating the orthotic with the post installed beneath it.

DETAILED DESCRIPTION OF THE INVENTION

The device of this invention includes a board or plate 10 having a flat upper surface 11. Flat upper surface 11 includes diverging lines 12 and 13 which may be painted or inked upon upper surface 11 but preferably are inherent lines formed between adjacent elements as will be described hereinafter.

A sheet or plate 15 of stiff material, preferably stainless steel, is mounted on board 10. The sheet 15 includes a portion 16 that is parallel to and in flat contact with board 11, a portion 17 which is a planar portion that is at an angle from the plane of portion 16 to subtend an angle "a" between portion 17 and the upper surface of board 10. The sheet 15 also includes a portion 18 and a portion 19 which respectively are at an angle from the upper surface of board 11 and flat against the upper surface of board 11 so that the intersecting planes of portion 18 and portion 19 also intersect at an angle such that the angle "a" is subtended between the lower surface of portion 18 and the upper surface of board 11. Planes 16 and 17 intersect along line 20 in a manner such that line 20 exactly overlays line 12 and the planes of portions 18 and 19 intersect along a line 21 which exactly overlays line 13. The lines of intersection of these planes preferably are emphasized by painting, inking or otherwise highlighting them. As a result of this construction, the planes of portion 17 and portion 18 intersect in a line 22 that is perpendicular to the edge 24 of the board 10.

In a preferred embodiment of the invention, sheet 15 is removably attached to board 11 by means such as bolts embedded within board 11 and fastened with wing nuts 24 and 25. Shims may be used in conjunction with the bolts to adjust the height of the post. In the preferred embodiment of the invention the board 11 is composed of a substructure 30 made of plywood, particle board or the like, that has a surface of plastic material such as Formica in two different colors or textures. The two end pieces of surface material 31, for example, may be white while the center portion of surface material 32 may be red or blue or some other dark color so that the lines 12 and 13 are inherently formed on board 11 whereby there is no need to re-paint them if they become worn off and in order to form a very narrow line so that the thickness of lines 12 and 13 will not become a judgment factor in the use of the device.

An orthotic device 35 is illustrated in place on the device of this invention. The orthotic device normally includes a heel cup portion 36 which has gradually raised surfaces and slightly elevated walls along the sides of the orthotic device. However, the front of the orthotic device at 37 is feathered to blend along a smooth line onto the insole of a shoe. The overall length from the back of the heel cup to the portion 37 is enough to reach from the heel of the patient to just short of the metatarsal arch.

In using the device of this invention, an orthotic 35 is positioned on the device in such a manner that the intersection of line 20 and the orthotic is approximately 5 millimeters inside the rearmost position of the orthotic, the term "inside" being with respect to inside of or outside of the patient's foot. The orthotic is also oriented so that line 12 will be tangent to the outermost edge of the orthotic. With the orthotic in this position and lying naturally on upper surface 11, the orthotic is held firmly in place, for example, by holding it with the thumb at the position 38. Immediately below position 38 the orthotic is a flat surface and it can be held in its natural orientation with respect to horizontal and without wobbling. With the orthotic held in place, with a thumb or a tool such as a clamp, a plastic material that hardens upon standing such as polymethylmethacrylate illustrated at 40 is placed beneath the orthotic by means such as a spatula. The plastic 40 is packed beneath the orthotic to fill the space beneath it but not to penetrate beneath the surface of the orthotic that is in contact with sheet 15. If necessary, the sheet 15 will be sprayed or otherwise coated with a release so that when the plastic 40 sets, the orthotic with the plastic post 40 fixed to it can easily be removed from sheet 15. Some trimming of the vertical walls of post 40 may be necessary for cosmetic purposes or to make it fit more easily into a shoe, however, the bottom surface of post 40 will be perfectly formed with intersecting planes at the proper angle and with the line of intersection between the angular planes in exactly the correct direction.

For the overwhelming majority of patients requiring orthotics the angle "a" shown in FIG. 1 is 4 degrees. For virtually all patients the rear post should be installed with the angle "b" between the front edge of board 10 and line 12 and 13 at about 70 degrees. When an orthotic must be manufactured for a patient employing an angle "a" other than 4 degrees, the sheet 15 having an angle "a" at 4 degrees may be removed and an auxiliary sheet 15 having an angle "a" appropriate to the particular patient may be installed.

What is claimed is:

1. A biplane posting device comprising:
a board having a flat upper surface, a front edge and a rear edge and indicia forming a straight line diverging from the rear edge and toward the front edge at a first angle; and
a thin plate overlying said upper surface, said thin plate having a planar portion parallel to said surface and in contact with it and a planar portion diverging from said upper surface at a second angle and with the line formed by the intersection of said planar surfaces overlying said straight line.

2. The device of claim 1 wherein said first angle is about 70 degrees.

3. The device of claim 1 wherein said second angle is about 4 degrees.

4. The device of claim 1 wherein said second angle is about 2 degrees.

5. The device of claim 1 wherein said second angle is about 6 degrees.

6. The device of claim 1 wherein said thin plate is removably attached to the upper surface of said board.

7. The device of claim 1 wherein said flat upper surface is comprised of at least two pieces of coating material connected to said board and abutting each other to form said straight line at their abutment.

8. The device of claim 1 wherein said surface has two straight lines at said first angle diverging from the rear edge toward the front edge, said thin plate has two planar portions diverging from said upper surface and the two diverging planar portions intersect in a line bisecting the angle between said diverging lines.

9. The device of claim 7 wherein said two pieces of coating material are of different colors.

* * * * *